United States Patent
Qualliotine et al.

(10) Patent No.: US 6,416,322 B2
(45) Date of Patent: Jul. 9, 2002

(54) POWDERING ATTACHMENT FOR APPLYING POWDER TO TOOTH SURFACES

(76) Inventors: Danny W. Qualliotine, 956 E. 10th St.; Otto Armand Qualliotine, 2312 Donna Ct., both of Greenville, NC (US) 27858

( * ) Notice: Subject to any disclaimer, the term of this patent is extended or adjusted under 35 U.S.C. 154(b) by 0 days.

(21) Appl. No.: 09/898,309

(22) Filed: Jul. 3, 2001

(51) Int. Cl.$^7$ ................................................ A61C 3/02
(52) U.S. Cl. ...................................................... 433/88
(58) Field of Search ............................ 433/80, 88, 82, 433/87

(56) References Cited

U.S. PATENT DOCUMENTS

| | | | | |
|---|---|---|---|---|
| 3,164,153 A | * | 1/1965 | Zorzi ............................ | 433/88 |
| 4,522,597 A | * | 6/1985 | Gallant ......................... | 433/216 |
| 4,741,697 A | * | 5/1988 | Herbison ...................... | 433/80 |
| 5,120,219 A | * | 6/1992 | De Farcy ...................... | 433/88 |
| 5,286,201 A | * | 2/1994 | Yu ................................ | 433/80 |
| 5,944,521 A | | 8/1999 | Lawler | |
| 6,099,306 A | | 8/2000 | Lawler | |

OTHER PUBLICATIONS

Pages from PowderMeister website printed Dec. 15, 2000; www.powdermeister.com/product.html (3 pages).

Information provided with Powder Meister including: 1. *Directions for Using the Powder Meister*™ (total of 3 pages); 2. *Frequently Asked Questions*; and 3. *Helpful Web Sites for CEREC 2 Users*.

Beuttell, Jeffrey, *Introduction to Cerec 3—A Guide for Beginning to Intermediate Users* (2000)—pp. 1 and 21–26.

Printout of catalog, p. 131 from American Dental Accessories catalog vol. 00–102 with description of the Powder Meister™ device. (2 pages), www.americandental.com.

Printout of Centrix catalog pp. 11 from Feb.–Mar. 2001 catalog showing Centrix Access® device use (2 pages), www.centrixdental.com.

\* cited by examiner

*Primary Examiner*—Cary E. O'Connor
(74) *Attorney, Agent, or Firm*—Daniels & Daniels, P.A.; Kevin E. Flynn

(57) ABSTRACT

A powdering attachment for applying powder to tooth surfaces is disclosed. Such an attachment is useful in operations such as preparations of a tooth before the use of dental equipment in the CEREC® family of products. The powdering attachment may be connected to a dry air syringe that is adapted to allow for the removable connection of dental accessories such as the powdering attachment. When connected to the dry air syringe, the control valve mechanism on the dry air syringe controls the air flow into the powdering attachment. An air tip assembly is given as an illustration of another dental accessory that may be attached to the modified dry air syringe.

22 Claims, 4 Drawing Sheets

POWDERING ATTACHMENT FOR APPLYING POWDER TO TOOTH SURFACES

BACKGROUND OF THE INVENTION

1. Technical Field

The disclosed device and method for use are in the field of dental tools.

2. Description of Prior Art

Restorative dental work includes a computer-aided method of making a replica tooth from a ceramic block through the use of a computer controlled milling machine. The replica tooth is made based on the tooth to be restored. This tooth is in the patient's mouth. The tooth is prepared by removal of silver fillings and any decayed material. The next step is to capture the shape of the tooth. In order to capture the digital image of the tooth by an imaging device, the tooth is made to contrast with the rest of the patient's mouth by coating the surfaces of the tooth with a suitable powder. This step is known as "powdering" the tooth. The imaging device is used to collect an image of the powdered tooth.

One such method uses a powder comprised of titanium dioxide and talc. The imaging system is a handheld infrared camera. Such a system is manufactured by Siemens Dental Products Division and distributed in the United States by Patterson Dental Supply, Inc. of St. Paul, Minn. under the name CEREC® 3.

Although the CEREC® 1, CEREC® 2 and now CEREC® 3 systems have been used for over a decade, the powdering devices are not well liked by the dentists that powder teeth. The powdering device is important because powdering is the first step towards successful completion of this restorative dental work. Problems with the application of the powder interfere with the attainment of suitable results in the imaging and digitizing steps. More specifically, the CEREC® 3 computer converts the light and dark areas of the image of the tooth into values representative of the height and depth of the surface of the tooth. This imaging process requires the application of a uniform coat of powder so that the entire target surface is covered. Too much powder is a problem as is too thin a coat. Thus, it is important to have a process that applies a uniform coat of powder to the target area.

One prior art device for this critical "powdering" step involved a pair of containers. One container held pressurized butane gas. The second container held the reflective powder. The device operated by releasing butane from the first container into the second container. The butane then carried reflective powder out of the second container and through a flexible tube towards the tooth to be coated. Such an applicator was distributed by Vita Zahnfabrik H. Rauter Graph and Co. KG of Bad Sackingen, Germany. Alternative suppliers of the butane propellant devices are Ivoclar™ (sold as ProCad powder) and Vita™ brand powder. Typically, these powdering techniques call for using a brush to apply imaging liquid to all the surfaces visible in the imaging step. The surfaces are blown dry after the imaging liquid is applied. Next the powder is sprayed on in a steady stream from a nozzle held about one or two centimeters from the tooth surface.

An alternative device is described in U.S. Pat. Nos. 5,944,521 and 6,099,306 for a Tooth Powdering Applicator issued to David Lawler. The Lawler device replaces the attached container of pressurized butane with a connection to a pressurized fluid. The outlet tube is rigid and curved. The Lawler device was designed to allow a dentist to use a single hand to hold the device and simultaneously rotate the outlet tube without use of the second hand of the dentist. The stated advantage was that the outlet tube can be rotated to allow the discharge stream from the powdering device to be aimed at various tooth surfaces without tilting the powder reservoir. Tilting the powder reservoir in the powdering device was thought to increase the risk of clumping the powder. Some embodiments of the Lawler device would include a valve on the powder container to allow the dentist to control the flow of fluid and powder with the hand holding the powdering device. Often a second foot controlled valve would be used in combination with the valve on the powder container. A device based on the Lawler patent is sold under the name PowderMeister™ by Powder Meister, Inc. of Bloomington, Ind.

Problems with Prior Art Solutions

The PowderMeister™ device requires an adjustment process each time it is used. The process includes closing the valve on the container using a thumbscrew so that no air can go into the powder container. Next, the foot control for the pressurized air is fully depressed. With the foot control remaining depressed, the thumbscrew is used to slowly open the valve on the container until the powder begins to flow. It is suggested that the initial spraying of powder within the mouth be directed to a tooth adjacent to the tooth to be powdered for imaging. This allows the clumps of powder to be discharged somewhere other than on the target tooth. Some clumps are attributed to storing the PowderMeister™ on its side or upside down so that excess powder enters the powdering tube. Water in the pressurized source of air poses a problem with the PowderMeister™ as the water will cause the powder to clump.

A second problem area with the PowderMeister™ device is the thumbscrew controlled air valve on the container. The amount of powder applied to the tooth is very sensitive to the position of the thumbscrew. That is, very little movement of the thumbscrew is needed to effect a change in the powder flow. Some dentists find that thumbscrews turn too freely. One corrective trick is to apply Super Glue™ to the threads of the thumbscrew air regulator to keep the thumbscrew from rotating too easily.

It is an object of this invention to provide a powdering device that is adapted to work with a valve that can be operated with one hand to apply a precise amount of airflow into the powder container.

It is an object of this invention to provide a powdering device that is easy to store in an upright position so that powder clumps do not form from non-upright storage.

It is an object of this invention to eliminate powder clumping caused by moisture in the pressurized air supply.

It is an object of this invention to allow the precision controlled dry air supply to be used in dental steps other than powdering to allow the dentist the option of purchasing less equipment.

It is an object of this invention to allow for quick changes between an air delivery function and the function of providing a dry air supply to the powdering device.

It is an object of this invention to provide these advantages while providing a device that is ergonomic such that is provides both accurate placement of powder while being comfortable to use.

These and other advantages of the present invention are apparent from the drawings and the detailed description that follows.

BRIEF SUMMARY OF DISCLOSURE

The improved powdering device disclosed herein is a powdering attachment designed to be used in conjunction with an existing piece of dental equipment known as a dry air syringe. The combination of the powdering attachment and the air syringe forms a powdering device. The dry air syringe is an ergonomic device with integral moisture filter designed for one-handed operation by the dentist. A precision valve on the top of the device allows the dentist to control the airflow by pressing with the thumb of the hand holding the air syringe. The powdering attachment is added to the outlet tube of the air syringe. No valve is needed on the powdering attachment. Nothing needs to be set. A foot-operated valve is not needed to turn the airflow on and off. The outlet tube on the powdering attachment rotates against resistance to allow alteration of the placement of the powder through use of the dentist's other hand. The powdering attachment is designed to allow quick removal of the outlet tube so that the outlet tube can be removed for sterilization after each patient.

The powdering attachment is designed to be easily removed from air syringe. Once disconnected from the air syringe, the powdering attachment is easy to store as it does not have an airline attached to it. When not used for powdering, the air syringe can be used for other operations such as porcelain bonding or any other bonding with dry air.

DESCRIPTION OF THE PREFERRED EMBODIMENT

Figure 1:
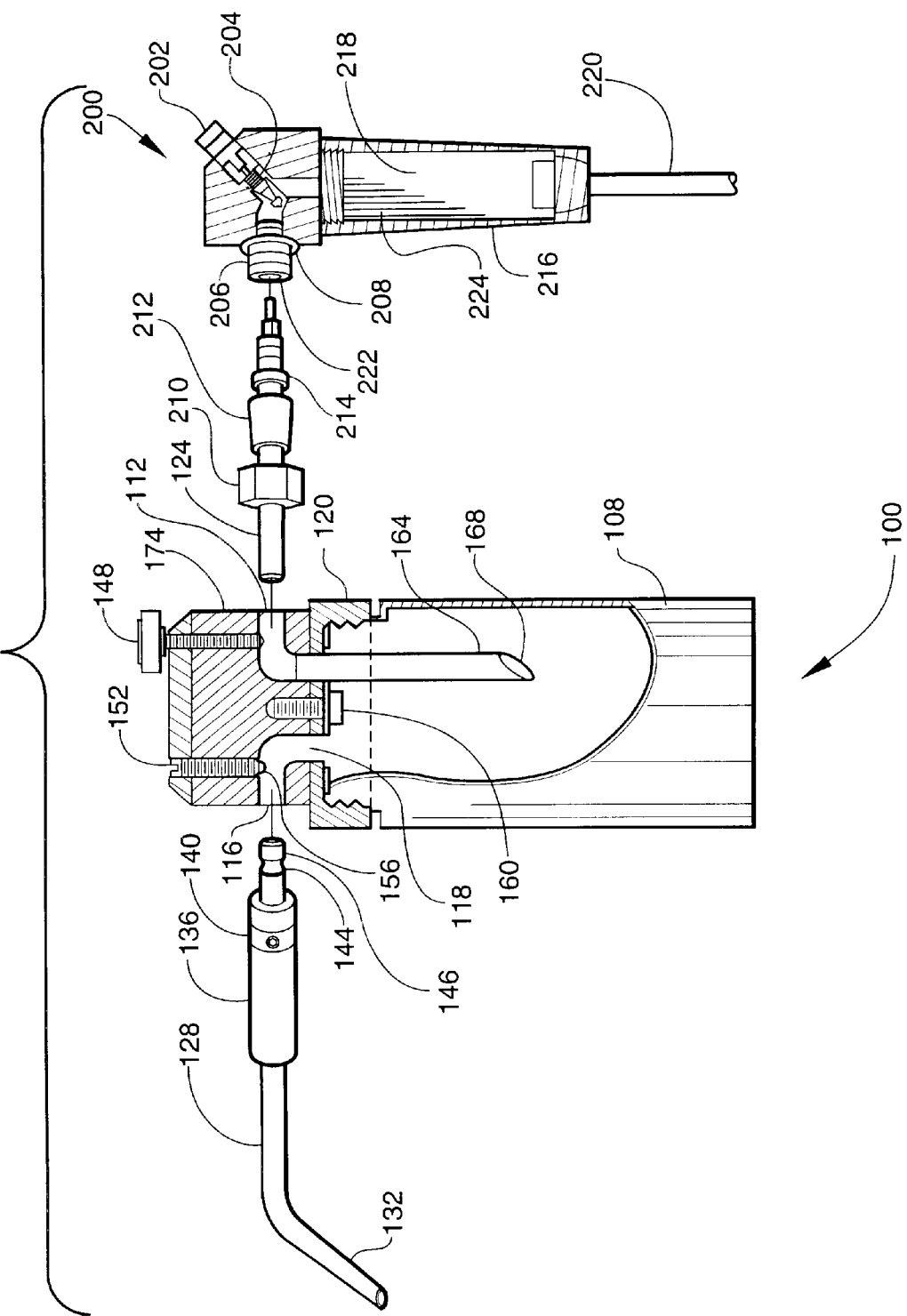
FIG. 1 is an exploded cross section of the tooth powdering device comprising the tooth powdering applicator and the dry air syringe.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art of which the invention relates.
Tooth Powdering Applicator Referring now more particularly to the drawings there is shown a tooth powdering applicator 100 including a powder holding container 108 for holding the reflective powder to be applied to the tooth to form a reflective coating thereon. The container has an air inlet 112 and a powder outlet 116 provided in the manifold block 174. A rigid inlet tube 124 has one end connected to air inlet 112 and the opposite end connected to a dry air syringe body 200 supplying filtered air. As used within this specification and the claims that follow, the term dry air is used in the context of dental devices. Thus the air does not need to be absolutely dry, simply dry enough to serve as "dry air".

Container 108 is hollow for holding a reflective powder. By way of illustration one such reflective powder is a mix of a titanium oxide and talc powder (CEREC® 2 POWDER by VIDENT available from Patterson Dental Supply, of St. Paul, Minn.). The manifold block 174 is attached to the threaded removable container cover 120 by the securing screw 160. Threaded removable container cover 120 is removed when the tooth powdering applicator 100 is to be filled with reflective powder.
Dry Air Syringe The dry air syringe body 200 is operated by button 202 to provide input to the control valve mechanism 204 to deliver precise amounts of filtered air into powder holding container 108 exiting bottom end of down tube 164 through bottom end tip 168. The dry air exiting through the bottom end tip 168 to agitate and transport tooth powdering powder out of the powder holding container through outlet channel 118.

The dry air syringe body 200 such as found in a bonding dry air syringe from American Dental Accessories, Inc. of Minneapolis, Minn. provides dry pressurized air. The body with its pistol type grip is ergonomically designed for comfortable use. The delivery of dry air helps prevent moisture contamination of the imaging powder. Optionally the dry air syringe body can be fitted with a quick disconnect (not shown) to allow the line connecting the dry air syringe to the air supply line to be quickly connected or disconnected.

The dry air syringe body is also an extremely useful tool when used with the optional air tip assemblies (described below). The quick disconnect feature with thumbscrew 148 allows for immediate conversion from a powdering device to a dry air bonding syringe useful in numerous dental procedures. The dry air syringe body can be conveniently located and stored in many places in and around a dental unit due to its standardized size and holding devices. This is an advantage when compared to other devices which have no suitable holders or holding fixtures. The present invention is not limited to use with a particular bonding dry air syringe. The present invention can be easily adapted by those of skill in the art to connect to other dry air syringes.

While the internal operation of the dry air syringe is not part of the present invention, for those not familiar with the operation of a dry air syringe, FIG. 1 shows additional detail. Air is provided to the air syringe body 200 through tubing connected to air supply outlet 220. The air enters the dry air syringe body 200 and passes through a moisture filter 218 such as cotton within a filter case 224 within the core of the handpiece handle 216. The dry air exits the moisture filter 218 and passes through the control valve mechanism 204 of the valve operated by push button 202. The traditional use of a dry air syringe body 200 would be with an air tip 226 (shown in FIG. 3). This air tip 226 would be attached to the threaded air outlet 222 of the dry air syringe body by tip holding nut 210, plastic tip cone 212, O-ring adapter nut 214, syringe tip adaptor nut 206, and O-ring 208.

Figure 3:
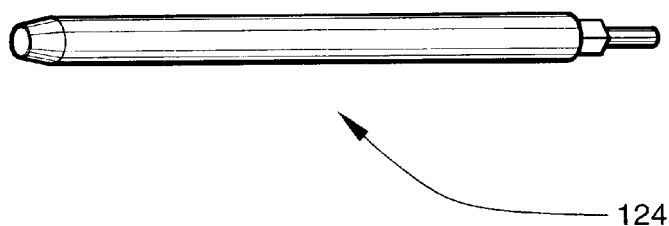
FIG. 3 shows how the rigid inlet tube 124 may be created from an air syringe air tip 226.
Figure 3A:
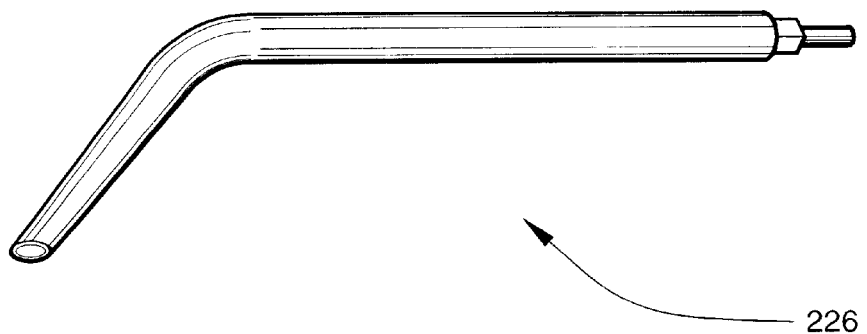
Figure 4:
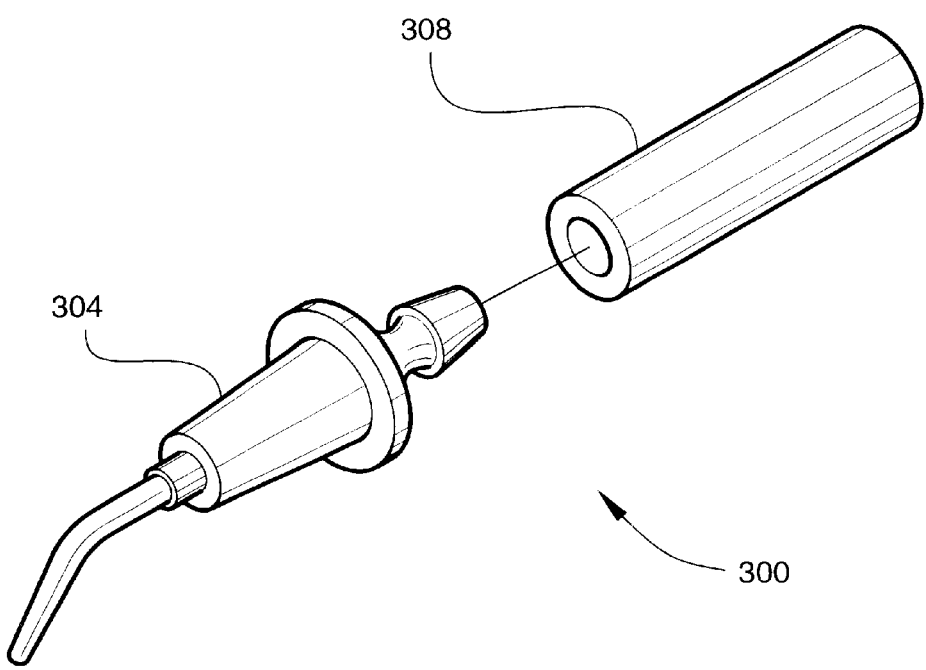
FIG. 4 shows details on the components of the air tip assembly 300.

When used in connection with the tooth powdering applicator 100, air tip 226 is replaced with rigid inlet tube 124. Optionally, rigid inlet tube 124 may be made by modifying an air tip 226. The comparison between air tip 226 and rigid inlet tube 124 is best seen in FIG. 3. As described below, the substitution of rigid inlet tube 124 for air tip 226 allows the dry air syringe body 200 to be used with a variety of dental accessories. The modified dry air syringe may be used with other dental accessories not discussed within this application which need a controlled source for dry air.
Air Tip Assembly While it would be possible to have one dry air syringe for providing dry air to the tooth powdering applicator and one for use in providing dry air to the mouth, it is advantageous to use one dry air syringe for both uses. Accordingly it is advantageous to be able to quickly shift from one function of the air syringe to the other. Disassembling elements 210, 212, 214, from threaded air outlet 222 in order to switch back and forth from air tip 226 and rigid inlet tube 124 would take too long as a dentist using a powdering device often needs to switch from powdering to blowing with air to powdering again in a span of twenty or thirty seconds. Thus, it is advantageous to use air tip assembly 300 shown in FIG. 4.

The dry air syringe may be used without the powdering device to deliver air precisely to areas that are difficult to reach, by attaching the air tip assembly 300. The tooth powdering applicator is quickly removed by turning inlet tube thumbscrew 148 (or an alternative hand manipulated fastening mechanism) to remove the rigid inlet tube 124 from the inlet to the tooth powdering applicator 100. The air tip assembly 300 slips over the end of rigid inlet tube 124 and stays on with a friction fit. The air tip assembly 300 can be made by adapting an ACCESS® Tip 304 sold be CENTRIX of Shelton, Connecticut as part number 290016 18ga, as part of its line if ACCESS® delivery syringes. The intended use of the ACCESS® Tip 304 is to deliver a silicon type impression material. The ACCESS® Tip 304 is combined with tubing shown as element 308 which can be cut to size from tubing stock from American Dental Accessories, Inc. The dry air syringe body 200 with rigid tube 124 and the air tip assembly 300 is very useful in dental bonding procedures where moisture free dry air is crucial.

Outlet Tube Assembly

Figure 2:
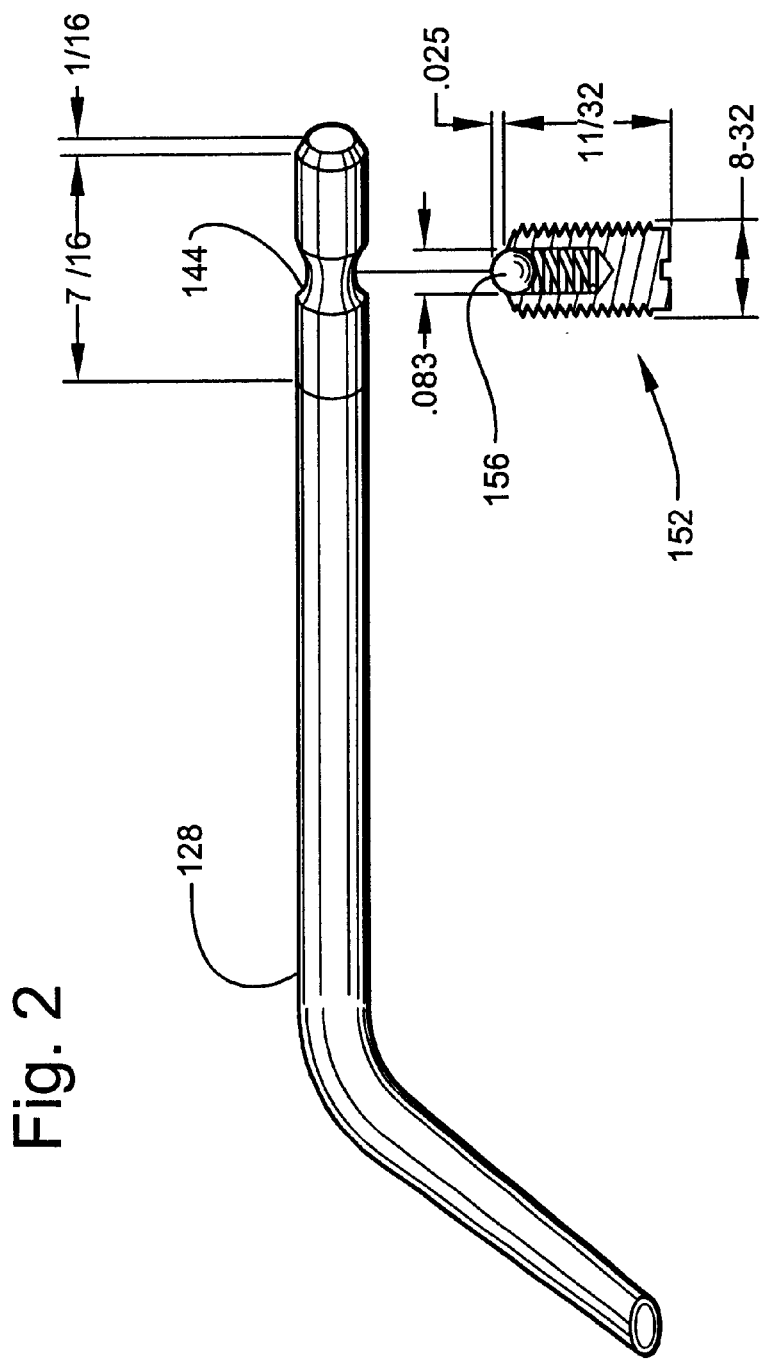
FIG. 2 shows additional details on the rigid outlet tube 128 and ball plunger assembly 152.

As shown in FIG. 1 and FIG. 2, outlet tube 128 is attached to the manifold block 174 by the interaction of a plunger ball 156 of the ball plunger assembly 152 fitting into a detent 144 allowing for easy removal for sterilization purposes. Such a plunger is well known to those of skill in the art and typically has a threaded shank with a spring loaded steel ball within a hollow core of the plunger. A preferred material for the ball plunger assembly 152 is stainless steel. A preferred material for the outlet tube 128 is a medical grade stainless steel, such as a 316 stainless steel. The outlet tube 128 is easily rotated while holding the powder container 108 upright and rotating the outlet tube 128 with the other hand. The preferred methods for connecting the rigid outlet tube 128 allow for endless rotation of the rigid outlet tube 128. In a preferred embodiment, the rigid outlet tube 128 is adapted to make it easier to grip. In one highly preferred embodiment, the rigid outlet tube 128 is placed inside of a silicon rubber sleeve 136 which is held in place by a locking ferrule 140. The snap fit of the rigid outlet tube 128 is an advantage for quick changing of the outlet tube and for removal for sterilization.

The outlet tube assembly is comprised of a rigid outlet tube 128. Rigid outlet tube 128 has a proximal end 146 connected to powder outlet 116 and a distal end 132 through which the powder is sprayed on the tooth. In a most preferred embodiment, the distal end 132 is arranged at an approximately 50-degree angle with respect to the to provide convenient access to all areas of the mouth. Note, that the invention is not limited to an approximately 50 degree angle as other angles between approximately 40 degrees and 90 degrees would work. The range of 45 to 75 degrees is thought to work better than 40 to 90 degrees with the most preferred angle at approximately 50 degrees. Note that as the outlet tube assembly is preferably set for quick connection/disconnection, an alternative embodiment would use two or more outlet tube assemblies with one assembly have a more severe angle than the other.

The tooth powdering applicator 100 can be easily removed (as described above) so that it can be stored upright. Storage of the tooth powdering applicator is simple in that there is no flexible tubing to be wrapped up or stored.

Loading and Use

The tooth powdering applicator 100 is loaded by first removing the removable container cover 120. Next, reflective powder (not shown) is added to the powder holding container 108. The height of the reflective powder should be below bottom end tip 168. Typically the reflective powder is added until it fills approximately one third of the powder holding container 108.

After filling the device with powder and attaching to compressed air line, it is aimed at a tooth that has been coated with suitable wetting agent causing the powder to stick as it is sprayed on the tooth. Care is taken to uniformly coat the tooth with a layer of reflective powder. The powder coats most uniformly when sprayed at a right angle to the surface you are coating. The delivery nozzle can be rotated to make it easier to spray the reflective powder on the various faces of the tooth.

Cleaning is accomplished by disassembling and blowing out with compressed air. The unit is disassembled. The air tip assembly 300 is placed on the dry air syringe. The dry air syringe and air tip is used to blow out each orifice in the disassembled unit. Generally the unit will not need to be rinsed with water unless the unit was contaminated by moisture. In that rare case, the unit can be washed and then completely dried before the next use.

Examples of preferred materials for the present invention include $8-36 \times 11/32$ stainless steel ball plunger; $6-32 \times 3/8$ stainless steel SHC screw; $6-32 \times 14$ stainless steel SHC screw; knurled knobs; medical grade stainless steel tubing; medical grade silicone tubing; $1/16$ inch tubing (brass); $1/8$ inch tubing (brass); $1/2$ inch aluminum bar (6061); and a medicine bottle.

Those skilled in the art will recognize that the methods and apparatus of the present invention has many applications and that the present invention is not limited to the specific examples given to promote understanding of the present invention. Moreover, the scope of the present invention covers the range of variations, modifications, and substitutes for the system components described herein, as would be known to those of skill in the art.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

We claim:

1. A tooth powdering applicator for use as an attachment to a dry air syringe having a dry air syringe control valve to apply powder carried by dry air output from the dry air syringe to a tooth, the tooth powdering applicator comprising:

A. An applicator body with integral cavity for holding tooth powdering powder;
   B. An air inlet to the applicator body;
   C. A means for connecting the air inlet of the applicator body to the dry air syringe such that the dry air output from the dry air syringe is in fluid communication with the air inlet of the applicator body;
   D. A down tube in fluid communication with the air inlet of the applicator body and with the cavity for holding tooth powdering powder such that dry air from the dry air syringe may pass through the air inlet of the applicator body and travel through and out of the down tube to agitate and transport tooth powdering powder out of the cavity holding tooth powdering powder through an outlet channel; and E. An outlet tube assembly in fluid communication with the outlet channel with an assembly inlet and an open distal end for directing the transported tooth powder towards a targeted tooth, the outlet tube assembly being removably connected to the applicator body, the removable outlet tube assembly capable of 360 degree rotation with respect to its connection to the applicator body.

2. The tooth powdering applicator of claim 1 wherein the means for connecting the applicator body to the dry air syringe includes connecting a syringe outlet tube to the dry air syringe wherein the syringe outlet tube is adapted for connecting to the air inlet of the applicator body.

3. The tooth powdering applicator of claim 1 wherein the removable outlet tube assembly is connected by to the applicator body through use of a detent to allow infinite rotation of the outlet tube assembly with respect to the applicator body.

4. The tooth powdering applicator of claim 1 wherein the path from air inlet of the applicator body to the outlet channel of the cavity is always free of obstruction from control value mechanisms such that control of the amount of dry air entering the cavity for holding tooth powdering powder is controlled by control mechanisms before the air inlet of the applicator body.

5. The tooth powdering applicator of claim 1 wherein the open distal end of the removable outlet tube assembly is not aligned with the assembly inlet wherein the non-alignment facilitates application of tooth powdering powder to various surfaces of the targeted tooth.

6. The tooth powdering applicator of claim 5 wherein the angle of non-alignment between the open distal end and the assembly inlet is in the range of approximately 40 degrees to approximately 60 degrees.

7. A tooth powdering applicator system for applying reflective powder to the various surfaces of a tooth comprising:
  A. a tooth powdering applicator comprising: a container for holding reflective powder to be applied to the tooth for form a reflective coating thereon, said container having a air inlet, a powder outlet, and a means for adding powder to the container;
  B. a dry air syringe comprising:
    i. a syringe body with a pistol type grip;
    ii. an air hose adapted for connection to a pressurized air source, the air hose connected to the syringe body;
    iii. a moisture filter within the syringe body, the moisture filter having an inlet and an outlet, the inlet to the moisture filter in fluid communication with the air hose;
    iv. a syringe body air outlet;
    v. a path from the outlet of the moisture filter to the syringe body air outlet; and
    vi. a control valve mechanism for selectively blocking the path from the outlet of the moisture filter to the syringe body air outlet wherein the control valve mechanism controls the amount of air sent to the syringe body air outlet; and
  C. a rigid inlet tube connecting the air outlet on the body of the air syringe to the air inlet of the container.

8. The tooth powdering applicator system of claim 7 further comprising a rigid outlet tube rotatably and removably connected to the powder outlet of the container such that the tooth powdering applicator system can be operated by using a first hand to hold the dry air syringe and operate the control valve mechanism; the rigid outlet tube may be rotated with respect to the powder outlet while the first hand holds the dry air syringe through use of a second hand.

9. The tooth powdering applicator system of claim 8 wherein the rigid outlet tube is connected to the powder outlet of the container through use of a ball and plunger assembly.

10. The tooth powdering applicator system of claim 8 wherein the rigid outlet tube has an inlet end and an outlet end, and the outlet end is not aligned with the inlet end so as to facilitate the application of reflective powder to the tooth.

11. The tooth powdering applicator system of claim 8 wherein the rigid outlet tube has with a sleeve to facilitate the rotation of the rigid outlet tube relative to the powder outlet.

12. The tooth powdering applicator system of claim 7 wherein the air inlet of the container comprises a down tube with a bottom end of the down tube such that air from the dry air syringe is routed through the down tube and exits the bottom end of the down tube to agitate and transport reflective powder out the powder outlet.

13. The tooth powdering applicator system of claim 7 wherein the control valve mechanism for controlling the amount of air sent to the syringe body air outlet receives input from a push button.

14. The tooth powdering applicator system of claim 13 wherein the push button is a thumb-operated push button located above the pistol type grip.

15. The tooth powdering applicator system of claim 7 wherein the rigid inlet tube connecting the syringe body air outlet to the air inlet of the container is connected through use of a hand manipulated fastening mechanism so that the rigid tube can be quickly released from the air inlet of the container.

16. The tooth powdering applicator system of claim 7 further comprising an air tip assembly adapted for use on the rigid inlet tube when the rigid inlet tube is not connected to the air inlet of the container so that the air syringe may be used to direct dry air into a specific location within a mouth of a dental patient.

17. A dry air syringe comprising:
  A. a syringe body with a pistol type grip;
  B. an air hose adapted for connection to a pressurized air source, the air hose connected to the syringe body;
  C. a moisture filter within the syringe body, the moisture filter having an inlet and an outlet, the inlet to the moisture filter in fluid communication with the air hose;
  D. a syringe body air outlet;
  E. a path from the outlet of the moisture filter to the syringe body air outlet;
  F. a control valve mechanism for selectively blocking the path from the outlet of the moisture filter to the syringe body air outlet, wherein the control valve mechanism controls the amount of air sent to the syringe body air outlet; and
  G. a rigid tube with a first end and a second end, the first end adapted for reversible connection to the syringe body air outlet, the second end adapted for connection to a dental accessory wherein the outer surface of the rigid tube is beveled at the second end to facilitate insertion into the dental accessory.

18. A dry air syringe comprising:
  A. a syringe body with a pistol type grip;
  B. an air hose adapted for connection to a pressurized air source, the air hose connected to the syringe body;
  C. a moisture filter within the syringe body, the moisture filter having an inlet and an outlet, the inlet to the moisture filter in fluid communication with the air hose;

D. a syringe body air outlet;

E. a path from the outlet of the moisture filter to the syringe body air outlet;

F. a control valve mechanism for selectively blocking the path from the outlet of the moisture filter to the syringe body air outlet, wherein the control valve mechanism controls the amount of air sent to the syringe body air outlet;

G. a rigid tube with a first end and a second end, the first end adapted for reversible connection to the syringe body air outlet, the second end adapted for connection to a dental accessory; and H. an air tip assembly dental accessory attached to the dry air syringe by inserting the rigid tube into one end of the air tip assembly tubing adaptor.

19. A dry air syringe comprising:

A. a syringe body with a pistol type grip;

B. an air hose adapted for connection to a pressurized air source, the air hose connected to the syringe body;

C. a moisture filter within the syringe body, the moisture filter having an inlet and an outlet, the inlet to the moisture filter in fluid communication with the air hose;

D. a syringe body air outlet;

E. a path from the outlet of the moisture filter to the syringe body air outlet;

F. a control valve mechanism for selectively blocking the path from the outlet of the moisture filter to the syringe body air outlet, wherein the control valve mechanism controls the amount of air sent to the syringe body air outlet;

G. a rigid tube with a first end and a second end, the first end adapted for reversible connection to the syringe body air outlet, the second end adapted for connection to a dental accessory; and H. a tooth powdering applicator dental accessory attached to the dry air syringe by inserting the rigid tube into an air inlet section of the tooth powdering applicator and then tightening a hand manipulated fastening mechanism, such that the control valve mechanism of the dry air syringe is used to control the amount of dry air provided to the air inlet of the tooth powdering applicator and thus control the amount of air carrying tooth powder that is emitted from the tooth powdering applicator.

20. A method of applying a powder to a tooth comprising the steps of:

A. Preparing the tooth powder applicator system, the step of preparing the tooth powder applicator system comprising the acts of:

Placing a quantity of powder into a cavity in a tooth powdering applicator;

Connecting a removable, rotatable, rigid outlet tube to an outlet of the tooth powder applicator, the outlet of the tooth powder applicator in fluid communication with the cavity; the rigid and outlet tube having a first end connected to an outlet of the tooth powdering applicator and a distal second end, the second end not aligned with the first end; and Inserting an end of a syringe outlet tube of a dry air syringe into an air inlet of the tooth powder applicator, the air inlet in fluid communication with the cavity so that operation of a control valve mechanism on the dry air syringe sends dry air out the end of the syringe outlet tube into the inlet of the tooth powder applicator, into the cavity where the dry air agitates the powder and transports a portion of the powder out the outlet of the tooth powder applicator, through the rigid outlet tube towards the tooth;

B. Holding the dry air syringe with a first hand and applying a controlled flow of dry air and powder to a tooth surface; and C. Altering the direction of the controlled flow of dry air and powder by rotating the rigid outlet tube relative to the outlet of the tooth powder applicator with a second hand while continuing to hold the dry air syringe with the first hand.

21. The method of claim 20 wherein the act of inserting an end of the syringe outlet tube into the tooth powder applicator includes tightening a hand manipulated fastening mechanism.

22. The method of claim 21 further comprising of:

A. un-tightening the hand manipulated fastening mechanism after applying powder to the tooth surface;

B. removing the tooth powdering applicator from the syringe outlet tube;

C. inserting the end of the syringe outlet tube into a second dental accessory; and D. using the dry air syringe to provide dry air for use with the second dental accessory.

* * * * *